(12) United States Patent
Miyoshi et al.

(10) Patent No.: US 11,642,369 B2
(45) Date of Patent: May 9, 2023

(54) METHOD FOR ENHANCING EXPRESSION OF ANTIOXIDANT IN EPIDERMIS

(71) Applicant: J-Network, Inc., Huntington Beach, CA (US)

(72) Inventors: Tatsuro Miyoshi, Huntington Beach, CA (US); Brian Charles Keller, Huntington Beach, CA (US); Akira Kodama, Huntington Beach, CA (US)

(73) Assignee: J-Network, Inc., Huntington Beach, CA (US)

( * ) Notice: Subject to any disclaimer, the term of this patent is extended or adjusted under 35 U.S.C. 154(b) by 101 days.

(21) Appl. No.: 17/398,766

(22) Filed: Aug. 10, 2021

(65) Prior Publication Data

US 2022/0160755 A1    May 26, 2022

(30) Foreign Application Priority Data

Nov. 20, 2020    (JP) .............................. JP2020-193681

(51) Int. Cl.

| | |
|---|---|
| *A61K 31/765* | (2006.01) |
| *A61P 17/18* | (2006.01) |
| *A61P 17/16* | (2006.01) |
| *A61K 31/77* | (2006.01) |
| *A61Q 17/04* | (2006.01) |
| *A61Q 19/08* | (2006.01) |
| *A61K 8/86* | (2006.01) |

(52) U.S. Cl.
CPC ............ *A61K 31/765* (2013.01); *A61K 31/77* (2013.01); *A61P 17/16* (2018.01); *A61P 17/18* (2018.01); *A61Q 17/04* (2013.01); *A61Q 19/08* (2013.01); *A61K 8/86* (2013.01)

(58) Field of Classification Search
CPC ...... A61K 31/765; A61K 47/60; A61K 47/62; A61K 47/6903; A61K 8/86; A61Q 19/007; A61Q 19/08; A61P 17/16; A61P 17/18

See application file for complete search history.

(56) References Cited

U.S. PATENT DOCUMENTS

| | | |
|---|---|---|
| 6,495,596 B1 | 12/2002 | Keller |
| 6,998,421 B2 | 2/2006 | Keller |
| 2008/0317836 A1* | 12/2008 | Dorogi .................... A61P 17/00 424/630 |

(Continued)

FOREIGN PATENT DOCUMENTS

| | | |
|---|---|---|
| JP | 4497765 B2 | 7/2010 |
| JP | 6297737 B1 | 3/2018 |
| JP | 6860739 B1 | 4/2021 |

*Primary Examiner* — Savitha M Rao
(74) *Attorney, Agent, or Firm* — Kolitch Romano Dascenzo Gates LLC

(57) ABSTRACT

To enhance expression of an antioxidant-related substance in an epidermis by using a diacylglycerol PEG adduct, a method for enhancing expression of an antioxidant-related substance in an epidermis is provided which includes applying a diacylglycerol PEG adduct to the epidermis as an active ingredient. The antioxidant-related substance is an oxidative stress response gene, an antioxidant enzyme, or an antioxidant protein. The diacylglycerol PEG adduct is selected from the group consisting of PEG-12 glycerol dimyristate (GDM12), PEG-12 glycerol distearate (GDS12), PEG-23 glycerol distearate (GDS23), PEG-23 glycerol dipalmitate (GDP23), and PEG-12 glycerol dioleate (GDO12).

12 Claims, 10 Drawing Sheets

(56) References Cited

U.S. PATENT DOCUMENTS

2011/0040113 A1* 2/2011 Wu ................... A61K 47/6911
                                                    568/679
2018/0371047 A1* 12/2018 Ticho ..................... C12N 15/52

* cited by examiner

METHOD FOR ENHANCING EXPRESSION OF ANTIOXIDANT IN EPIDERMIS

FIELD

The present disclosure relates to a method for enhancing expression of an antioxidant in an epidermis.

INTRODUCTION

Vesicles composed of a phospholipid and a surfactant are known and are also referred to as liposomes. Japanese Patent No. 4497765 presents a preparation method for causing spontaneous formation of vesicles by using a lipid mainly containing a diacylglycerol polyethylene glycol adduct (hereinafter, also called "diacylglycerol PEG adduct") in place of a phospholipid and mixing it with water or a surfactant. Such vesicles are used in a drug delivery system that delivers a target substance, for example, a protein or an antibody, to cells in a living organism by encapsulating the substance in the vesicles or binding the substance to the surface of the vesicles.

A vesicle containing a diacylglycerol PEG adduct as a lipid has a form in which the surface thereof is covered by a hydrophilic PEG chain, and is excellent in permeability to a living organism and stability in blood. Japanese Patent No. 6297737 describes that a charged element is made to bind to the surface of vesicles containing a diacylglycerol PEG adduct to positively charge the vesicles, thereby improving permeability of the vesicles to a stratum corneum of an epidermis and retention of the vesicles in the stratum corneum.

Vesicles in a drug delivery system are recognized simply as carriers of a target substance. The vesicles are finally decomposed into individual molecules in a living organism, but the action of the molecules themselves constituting the vesicles in the living organism is not well known. U.S. Pat. Nos. 6,998,421 and 6,495,596 disclose some actions of a diacylglycerol PEG adduct in a living organism. According to the disclosure, the diacylglycerol PEG adduct binds to phospholipase A and cyclooxygenase-2 in the living organism to inhibit these enzymes, thereby exerting an action of suppressing pain, fever, and inflammation. However, there are many mechanisms for suppressing inflammatory pathways other than this reduction of inflammation and the like by inhibition of phospholipase A and cyclooxygenase-2. As for the other inflammation suppression mechanisms, the action of the diacylglycerol PEG adduct in the living organism has not been known yet.

SUMMARY

An object of the present disclosure is to take advantage of a newly found property of a diacylglycerol PEG adduct, in particular, to enhance expression of an antioxidant in an epidermis. In order to achieve the above object, the present disclosure provides the following constitution.

An aspect of the present disclosure provides a method for enhancing expression of an antioxidant in an epidermis, comprising applying a diacylglycerol PEG adduct to a human epidermis as an active ingredient, wherein the diacylglycerol PEG adduct is represented by

[Chemical formula 1]

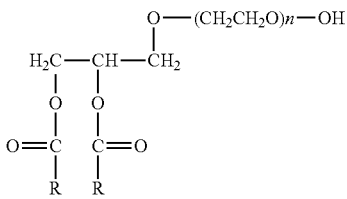

where the number of carbons in R in a long-chain fatty acid is in a range of 11 to 23 and n in a polyethylene glycol chain is in a range of 11 to 46.

Preferably, the diacylglycerol PEG adduct is selected from the group consisting of PEG-12 glycerol dimyristate (GDM12), PEG-12 glycerol distearate (GDS12), PEG-23 glycerol distearate (GDS23), PEG-23 glycerol dipalmitate (GDP23), and PEG-12 glycerol dioleate (GDO12).

Preferably, the diacylglycerol PEG adduct permeates an epidermis in a solution state.

Preferably, the diacylglycerol PEG adduct permeates an epidermis in a vesicle state.

Preferably, vesicles of the diacylglycerol PEG adduct have diameters in a range of 20 to 40 nm.

Preferably, the antioxidant is an oxidative stress response gene, and the oxidative stress response gene is Nrf-2.

Preferably, the antioxidant is an oxidative stress response gene, and the oxidative stress response gene is PPARG.

Preferably, the antioxidant is an antioxidant enzyme, and the antioxidant enzyme is one or more of the group consisting of NAD(P)H quinone reductase (NQO-1), catalase (CAT)), and heme oxygenase-1 (HMOX1).

Preferably, the antioxidant is an antioxidant protein, and the antioxidant protein is glutathione.

Preferably, the diacylglycerol PEG adduct is one of ingredients of cosmetics or pharmaceuticals, and the method for enhancing expression of an antioxidant in an epidermis further comprises applying the cosmetics or pharmaceuticals on a surface of a human skin.

The present disclosure further provides a method for suppressing epidermis damage caused by ultraviolet rays, using the method for enhancing expression of an antioxidant.

The present disclosure further provides a method for suppressing epidermis damage caused by air pollutants, using the method for enhancing expression of an antioxidant.

The present disclosure further provides a method for suppressing oxidation of hydroquinone in an epidermis, using the method for enhancing expression of an antioxidant.

According to the present disclosure, a method for enhancing expression of an antioxidant in a human epidermis, using a diacylglycerol PEG adduct as an active ingredient is realized.

Features, functions, and advantages may be achieved independently in various embodiments of the present disclosure, or may be combined in yet other embodiments, further details of which can be seen with reference to the following description and drawings.

DETAILED DESCRIPTION

Figure 1:
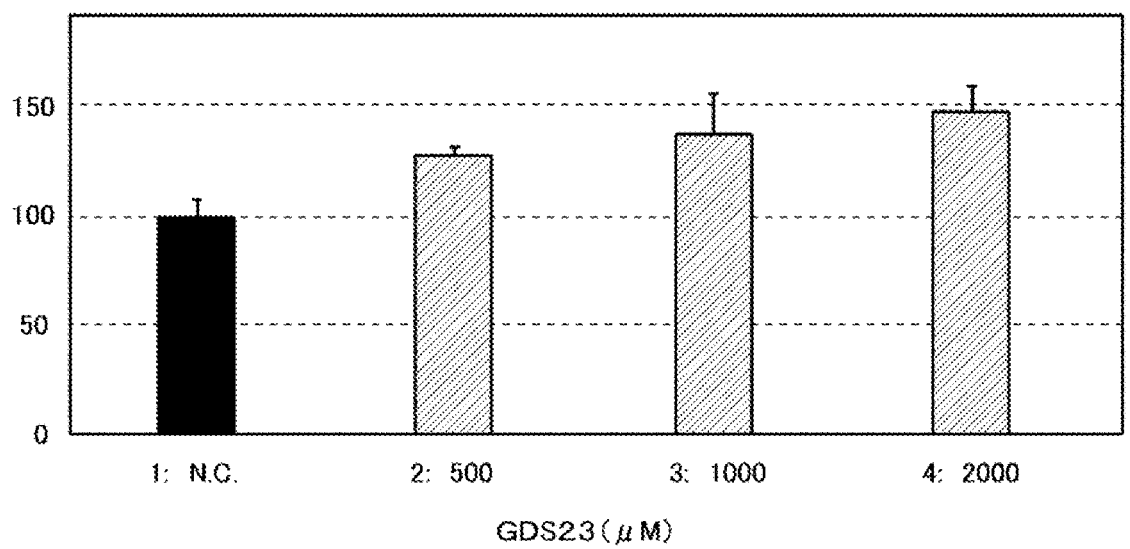
FIG. 1 is a graph illustrating an expression level of Nrf-2 for Samples 1 to 4.

Embodiments of the present disclosure are described below with reference to the drawings.

The present disclosure takes advantage of a newly found property of a diacylglycerol polyethylene glycol adduct (diacylglycerol PEG adduct). The newly found property is an action of enhancing expression of an antioxidant in a human epidermis.

A structural formula of a diacylglycerol PEG adduct, which is a lipid molecule according to the present disclosure, is schematically represented.

[Chemical formula 2]

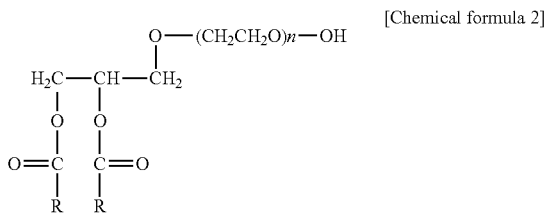

A diacylglycerol PEG adduct is composed of a glycerol skeletal part (CH2CHCH2) having three carbons, a PEG chain that is linear polyethylene glycol bonded to one terminal carbon of the three carbons in the skeletal part, and long-chain fatty acids (COOR) of the same type respectively bonded to the other two carbons of the three carbons. The PEG chain part is hydrophilic and the long-chain fatty acid parts are hydrophobic.

In the following description, when a specific diacylglycerol PEG adduct is described, it is referred to as "[PEG-n]+[glycerol]+[di]+[the name of long-chain fatty acid]" based on the type of long-chain fatty acid and n in the PEG chain. For example, when the long-chain fatty acid is myristic acid and n in the PEG chain is 12, the diacylglycerol PEG adduct is "PEG-12 glycerol dimyristate". The specific diacylglycerol PEG adduct may also be abbreviated.

The number of carbons in R in long-chain fatty acid can be in a range of 11 to 23. Examples of long-chain fatty acids within this range include myristic acid, palmitic acid, stearic acid, and oleic acid. Further, n in the PEG chain can be in a range of 11 to 46. Examples of a diacylglycerol PEG adduct related to the present disclosure are as follows. The melting point and the abbreviation are described in parentheses.

PEG-12 glycerol dimyristate (25.0° C.: GDM12)
PEG-12 glycerol distearate (40.0° C.: GDS12)
PEG-23 glycerol distearate (39.8° C.: GDS23)
PEG-23 glycerol dipalmitate (31.2° C.: GDP23)
PEG-12 glycerol dioleate (25.0° C.: GDO12)

An inflammatory pathway in a human living body involves oxidation of intracellular substances. In recent years, it has been often reported that skin troubles occur due to oxidative stress to cells caused by ultraviolet rays, air pollutants, and the like.

It is known that Nrf-2, which is an oxidative stress response gene, plays an important role in a defense mechanism against oxidative stress to a living organism. In the absence of oxidative stress, Nrf-2 that is a transcriptional activator binds to Keap-1 that is a protein, and is inactivated. When oxidative stress is applied to the living organism, Keap-1 is suppressed, so that Nrf-2 is activated. Activated Nrf-2 migrates into the nucleus of a cell and produces an antioxidant enzyme. Further, PPARγ, which is a protein, is also an antioxidant and enhances the antioxidative activity of a cell by mutually stimulating with Nrf-2.

The inventors found that expression of Nrf-2 and PPARγ, which are antioxidants in a human epidermis, is enhanced by applying a diacylglycerol PEG adduct to the epidermis. In addition, the inventors found that antioxidant enzymes and antioxidant proteins produced by these antioxidants also increase. As specific antioxidant enzymes, it was confirmed that production of each of NAD(P)H quinone reductase (NQO-1), catalase (CAT), and heme oxygenase-1 (HMOX1) is enhanced. As a specific antioxidant protein, it was confirmed that production of glutathione is enhanced. The action of enhancing expression of these antioxidants in epidermal cells is a newly found action regarding a diacylglycerol PEG adduct, and can be said as a novel property of the diacylglycerol PEG adduct. This novel action of the diacylglycerol PEG adduct is not merely physical protection for the epidermis surface, but is an action exerted in epidermal cells. It is considered that the antioxidant effect in the epidermis provided by this novel property can reduce skin troubles due to various types of oxidative stress from outside.

The present disclosure takes advantage of this newly found property of the diacylglycerol PEG adduct, thereby providing a method for enhancing expression of an antioxidant in an epidermis which includes applying the diacylglycerol PEG adduct to a human epidermis as an active ingredient.

In the present disclosure, when the diacylglycerol PEG adduct is applied to the human epidermis, the diacylglycerol PEG adduct may be used singly or in combination of two or more thereof.

According to the present disclosure, the diacylglycerol PEG adduct that has reached inside the epidermis expresses more antioxidants in the epidermis than in the absence of the diacylglycerol PEG adduct, thereby making it possible to reduce or prevent cell damage in the epidermis due to oxidative stress from outside, for example, ultraviolet rays or air pollutants. This effect was confirmed by tests described later.

Further, the diacylglycerol PEG adduct that has reached inside the epidermis expresses more antioxidants in the epidermis than in the absence of the diacylglycerol PEG adduct, thereby making it possible to suppress oxidation of hydroquinone, which is contained in cosmetics as a skin-whitening ingredient, in the epidermis. As a result, it is possible to prevent cell damage caused by toxic benzoquinone produced by hydroquinone oxidation in the epidermis. This effect was also confirmed by the tests described later.

Therefore, according to the present disclosure, it is possible to provide cosmetics or pharmaceuticals containing a diacylglycerol PEG adduct as an active ingredient so as to enhance expression of an antioxidant in an epidermis. Further, according to the present disclosure, it is possible to provide a method for reducing or preventing cell damage in an epidermis, which uses a diacylglycerol PEG adduct as an active ingredient, so as to enhance expression of an antioxidant in the epidermis.

In one method for making the diacylglycerol PEG adduct reach inside the human epidermis, the diacylglycerol PEG adduct can be made to reach inside the epidermis in a solution state in which the diacylglycerol PEG adduct is dissolved in water or a predetermined solvent. For example, a diacylglycerol PEG adduct solution having a predetermined concentration is prepared using phosphate buffered saline (PBS(−)) as a solvent and the solution is applied to the skin surface, whereby the diacylglycerol PEG adduct can be made to permeate the epidermis. The applied solution permeates a stratum corneum as the uppermost layer, and further permeates a stratum granulosum below the stratum corneum. In each layer in the epidermis that the diacylglycerol PEG adduct permeates, the diacylglycerol PEG adduct enhances expression of an antioxidant originally present in that layer.

In a preferable method, it is possible to make the diacylglycerol PEG adduct reach inside the human epidermis in a vesicle state. Such vesicles are formed as closed spherical shells composed of a double layer of the diacylglycerol PEG adduct or a multilayer in which the double layers are stacked, and a hydrophilic PEG chain is arranged in the surface of the outermost layer. The vesicles of the diacylglycerol PEG adduct are prepared and are applied on the skin surface, whereby the diacylglycerol PEG adduct can be made to permeate the epidermis. After reaching inside the epidermis, the vesicles are decomposed and separated into individual molecules, whereby the action of the diacylglycerol PEG adduct itself can be exerted.

In a conventional drug delivery system, a diacylglycerol PEG adduct as a material of vesicles has been considered as a mere carrier of a target substance. Meanwhile, the present disclosure uses a diacylglycerol PEG adduct itself as an active ingredient. Therefore, the present disclosure does not require a target substance to be incorporated into vesicles in a usual drug delivery system, basically. According to the present disclosure, vesicles formed by mixing water and the diacylglycerol PEG adduct only are made to permeate the epidermis, thereby making the diacylglycerol PEG adduct itself function as an expression enhancer for the antioxidant in the epidermis.

Some diacylglycerol PEG adducts spontaneously form vesicles by being mixed with water at a predetermined temperature (see Japanese Patent Nos. 4497765 and 6297737). For example, a suspension of GDM12 or GDO12 vesicles can be obtained by mixing and stirring 2 mass % of GDM12 or GDO12 in 98 mass % of deionized water at room temperature. In another example, a suspension of GDS12 or GDS23 vesicles can be obtained by dissolving 2 mass % of GDS12 or GDS23 at a temperature of 45° C. to 55° C. and then mixing and stirring it in 98 mass % of deionized water at a temperature of 45° C. to 55° C. In further another example, a suspension of GDP23 vesicles can be obtained by dissolving 2 mass % of GDP23 at 37° C. and then mixing and stirring it in 98 mass % of deionized water at 37° C. The vesicles are stable even when the suspension obtained at a temperature above room temperature is cooled to room temperature.

Also in a case of using vesicles formed by mixing and stirring the diacylglycerol PEG adduct and an aqueous solution of any of various substances in place of water as still another example, if this case is also included in the scope of the present disclosure, the substance contained in the aqueous solution can have another function.

The size of the typical vesicles formed by the diacylglycerol PEG adduct is, for example, about 100 to 300 nm in diameter. Tests described later showed that refined vesicles, in particular, with diameters in a range of 20 to 40 nm exhibit a satisfactory antioxidant effect. This result is considered to be due to satisfactory permeability of the refined vesicles. Such refined vesicles can be obtained, for example, by mixing the diacylglycerol PEG adduct with squalane and cholesterol that are other lipids (details will be described later).

The scope of the present disclosure also covers, as still another example, a case of modifying the surface of the vesicles formed by mixing and stirring water or the aqueous solution and the diacylglycerol PEG adduct with a charged element, for example, a cationic surfactant, and using such vesicles. Japanese Patent No. 6297737 describes that positively charged vesicles are excellent, in particular, in permeability to an epidermis and retention in the epidermis.

Cosmetics or pharmaceuticals containing a diacylglycerol PEG adduct as an active ingredient can be provided in various forms including, for example, an aqueous solution, emulsion, gel, and cream.

A relation among application of a diacylglycerol PEG adduct to an epidermis, an antioxidant in the epidermis, and oxidative stress is presented by test data below.

(1) Test on Expression of Oxidative Stress Response Gene and Antioxidant Enzyme

After samples were prepared using normal human epidermal melanocytes, RNA was extracted, and expression and amplification of genes of each of target substances (Nrf-2, PPARG, NQO-1, CAT, and HMOX1) were checked by real-time PCR. PPARG is the genetic code of the protein PPARγ and is one of oxidative stress response genes.

(1-1) Test Method

Normal human epidermal melanocytes (NHEM: from Kurabo Industries Ltd.) were seeded at a cell density of $3.0 \times 10^4$ cells/well in a 96-well culture plate using a medium (DermaLife (registered trademark) M Comp kit medium: from Kurabo Industries Ltd.). Subsequently, the cells were cultured at 37° C. under 5% carbon dioxide for 24 hours.

Thereafter, the media were replaced with media to which Samples 1 to 4 described below were respectively added, and the cells were cultured at 37° C. under 5% carbon dioxide for 6 hours.

Sample 1 is a control (no GDS23 added). Samples 2 to 4 are different from one another in the amount of GDS23.
Sample 1: Control (N.C.)
Sample 2: GDS23 (500 μM)
Sample 3: GDS23 (1000 μM)
Sample 4: GDS23 (2000 μM)

Thereafter, RNA was extracted from the cultured cells for each sample. Reverse transcription of the extracted RNA was performed to generate cDNA, and the quantity of mRNA of each target substance was determined by quantitative real-time PCR expression analysis. GAPDH (glyceraldehyde-3-phosphate dehydrogenase) was used as an internal standard. In the analysis, the mRNA expression level of each target substance was corrected with a value of the expression level of GAPDH as the internal standard in the same sample, and thereafter the correction value for each sample was calculated, assuming the correction value for the control as 100%.

(1-2) Test Results

FIGS. 1, 2, 3, 4, and 5 are graphs illustrating expression levels of Nrf-2, PPARG, NQO-1, CAT, and HMOX1 for Samples 1 to 4, respectively.

Figure 2:
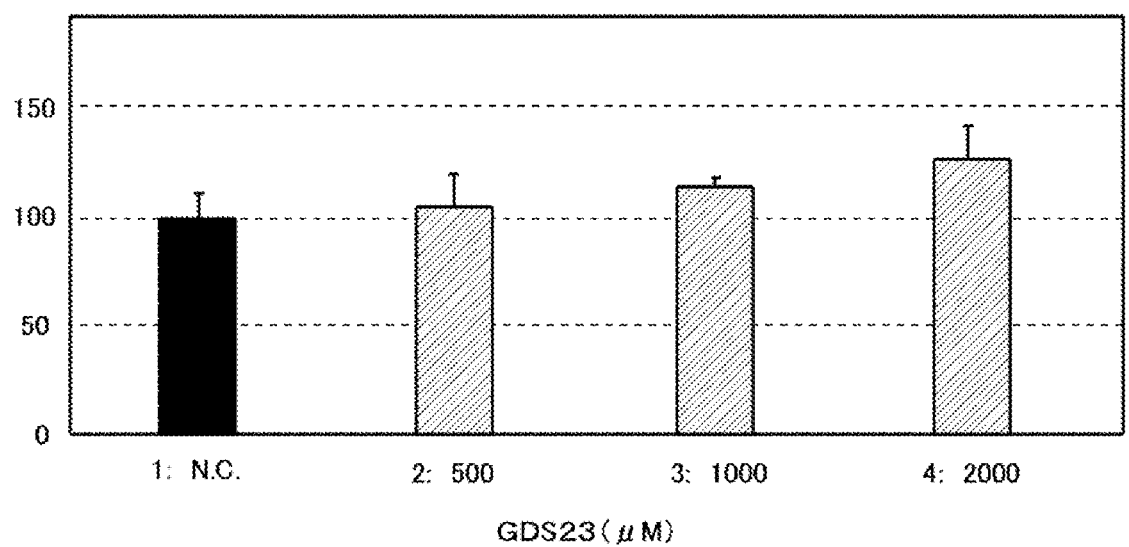
FIG. 2 is a graph illustrating an expression level of PPARG for Samples 1 to 4.
Figure 3:
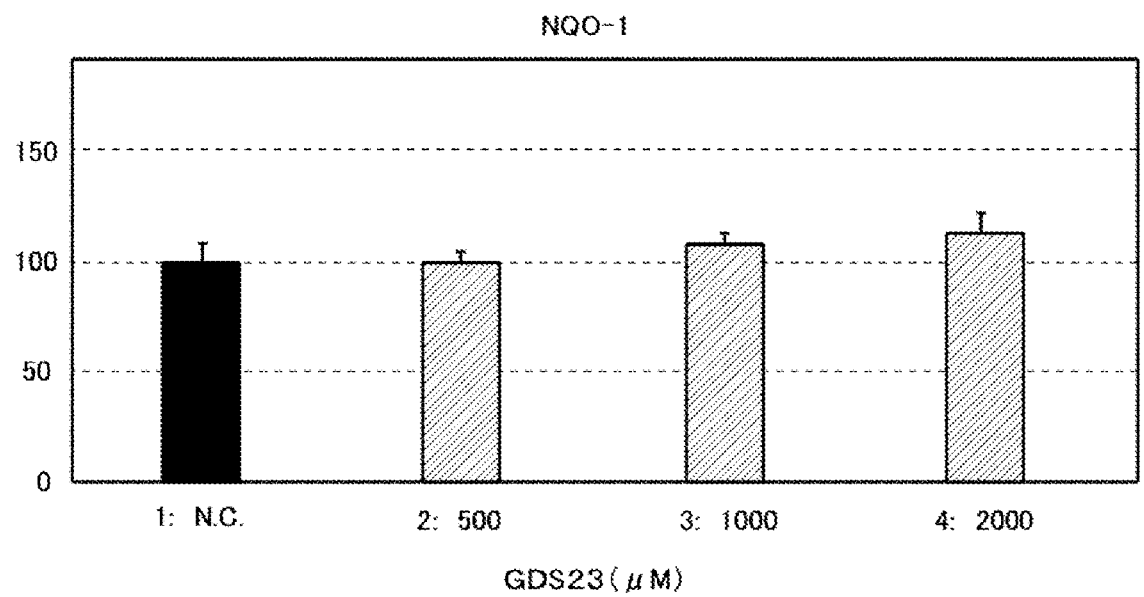
FIG. 3 is a graph illustrating an expression level of NQO-1 for Samples 1 to 4.
Figure 4:
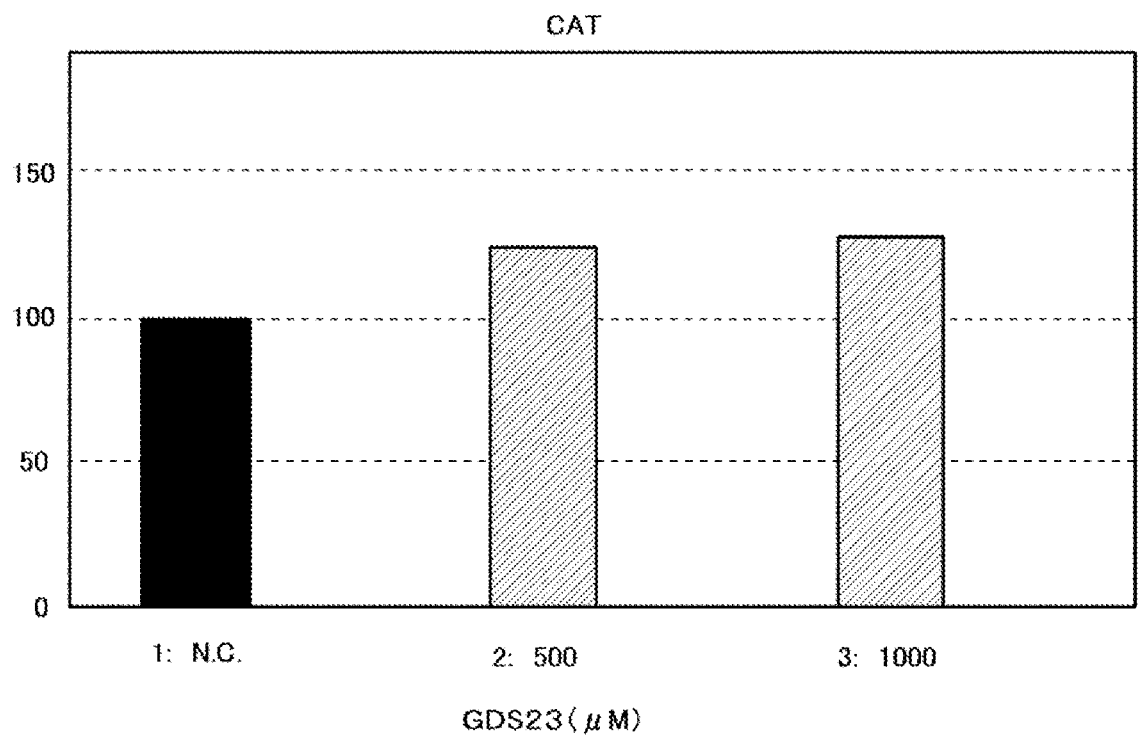
FIG. 4 is a graph illustrating an expression level of CAT for Samples 1 to 3.
Figure 5:
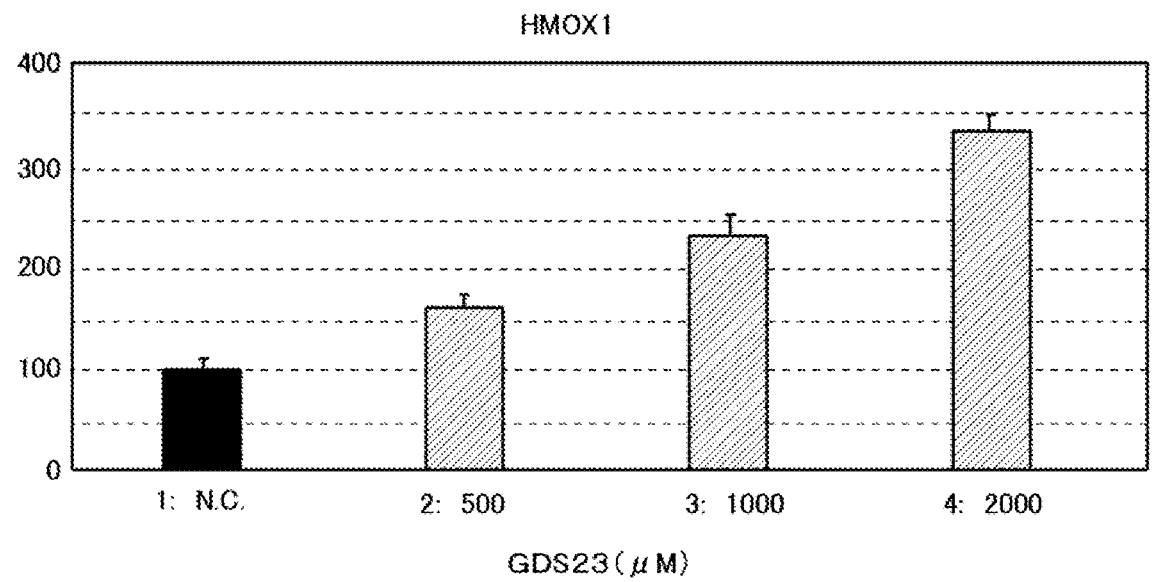
FIG. 5 is a graph illustrating an expression level of HMOX1 for Samples 1 to 4.

The results in FIGS. 1 and 2 show that treatment of epidermal melanocytes with GDS23 enhances expression of Nrf-2 and PPARG that are oxidative stress response genes. It is considered that when expression of Nrf-2 and PPARG is enhanced, production of antioxidant enzymes induced by them is also enhanced. FIG. 3 illustrates enhancement of NQO-1 that is an oxidoreductase. FIG. 4 illustrates enhancement of CAT that is an enzyme acting as a catalyst of a reaction to convert hydrogen peroxide into oxygen and water. Enhancement of HMOX1 in FIG. 5 shows enhancement of a heme-decomposition rate-determining enzyme and a cytoprotective protein that protects cells from damage caused by oxidative stress.

(2) Test on Expression of Antioxidant Protein

After samples were prepared using normal human epidermal melanocytes, the quantity of glutathione as an antioxidant protein in cells was checked.

(2-1) Test Method

Normal human epidermal melanocytes (NHEM: from Kurabo Industries Ltd.) were seeded at a cell density of $2.0 \times 10^4$ cells/well in a 96-well culture plate using a medium (DermaLife (registered trademark) M Comp kit medium: from Kurabo Industries Ltd.). Subsequently, the cells were cultured at 37° C. under 5% carbon dioxide for 24 hours. Thereafter, the media were replaced with the same type of media to which Samples 5 to 9 described below were respectively added, and the cells were cultured at 37° C. under 5% carbon dioxide for 24 hours.

Sample 5 is a control (no GDS23 added). Samples 6 to 9 are different from one another in the amount of GDS23.
Sample 5: Control (N.C.)
Sample 6: GDS23 (500 μM)
Sample 7: GDS23 (1000 μM)
Sample 8: GDS23 (2000 μM)
Sample 9: GDS23 (4000 μM)

Thereafter, for each sample, the protein quantity in epidermal melanocytes and the quantity of total glutathione (GSH+GSSG) were determined by a glutathione reductase recycling method, using an assay kit (TaKaRa BCA Protein Assay Kit: from Takara Bio Inc.). The total quantity of glutathione per protein quantity was obtained from the protein quantity and the total quantity of glutathione determined for each sample, and then an increased ratio for each sample was calculated when an increased ratio for the control was assumed as 100%.

(2-2) Test Results

Figure 6:
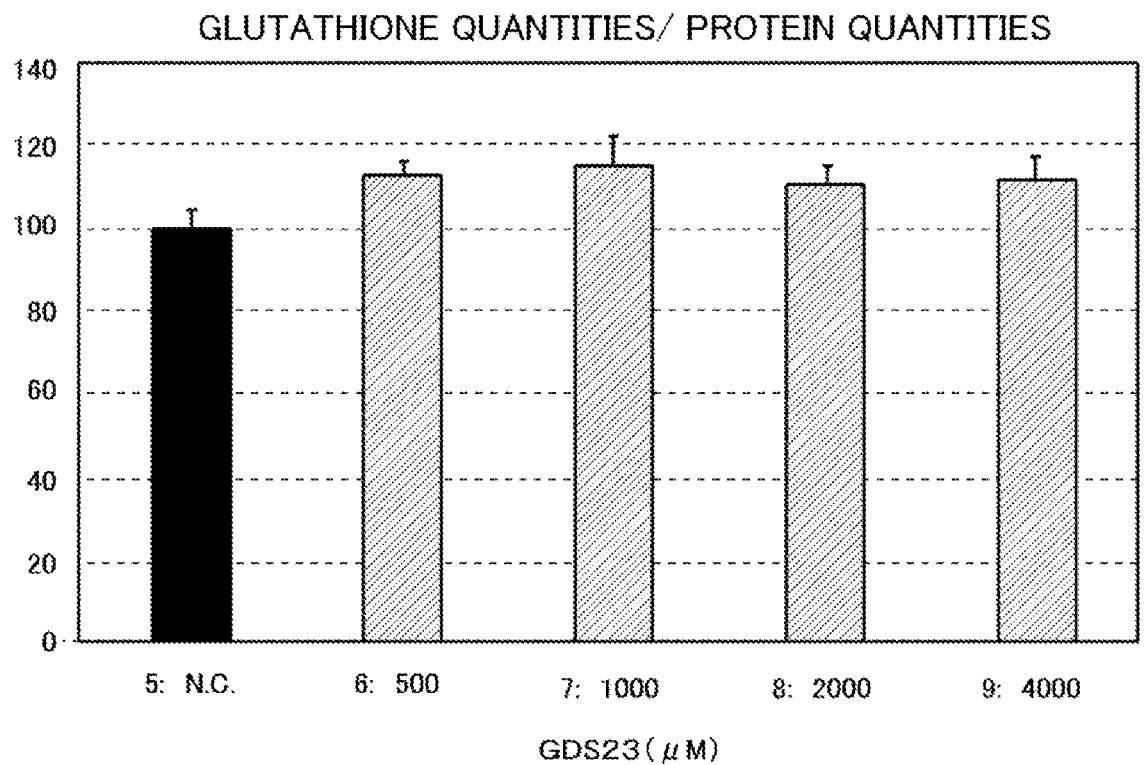
FIG. 6 is a graph illustrating a total quantity of glutathione per protein quantity in each of Samples 5 to 9.

FIG. 6 is a graph illustrating a total quantity of glutathione per protein quantity in each of Samples 5 to 9. It was confirmed from FIG. 6 that treatment of epidermal melanocytes with GDS23 promotes production of glutathione, which is a protein having a high antioxidative activity, in cells. Glutathione is produced by glutathione producing enzymes induced by Nrf-2 and/or PPARγ. Therefore, it was confirmed that enhancement of expression of Nrf-2 and/or PPARγ by GDS23 results in promotion of production of glutathione.

(3) Test 1 of Effect of Suppressing Ultraviolet Damage

The erythema reaction caused by ultraviolet rays is ultraviolet damage caused by short-wavelength ultraviolet rays (UVB) (290 to 320 nm), and is called sunburn. This sunburn is considered to be caused by active oxygen and prostaglandin E2. Therefore, a test to check a relation between UVB irradiation and a cell viability was conducted in order to show an effect of reducing ultraviolet damage by a diacylglycerol PEG adduct enhancing expression of an antioxidant in an epidermis.

(3-1) Test Method

Normal human epidermal keratinocytes (NHEK: from Kurabo Industries Ltd.) were seeded at a cell density of $2.0 \times 10^4$ cells/well in a 96-well culture plate using a KG2 medium (from Kurabo Industries Ltd.). Subsequently, the cells were cultured at 37° C. under 5% carbon dioxide for 24 hours. Thereafter, the media were replaced with the same type of media to which Samples 10 to 15, 16 to 19, and 20 to 24 described below were respectively added, and the cells were cultured at 37° C. under 5% carbon dioxide for 24 hours. Samples 10, 16, and 20 are controls (additive-free). Samples 11 to 15, 17 to 19, and 21 to 24 are different from one another in the type and/or concentration (mass %, solvent: HBSS(−)) of a diacylglycerol PEG adduct.
Sample 10: Control (N.C.)
Sample 11: GDS12 (0.03125%)
Sample 12: GDS12 (0.0625%)
Sample 13: GDS12 (0.125%)
Sample 14: GDS12 (0.25%)
Sample 15: GDS12 (0.5%)
Sample 16: Control (N.C.)
Sample 17: GDM12 (0.0125%)
Sample 18: GDM12 (0.025%)
Sample 19: GDM12 (0.05%)
Sample 20: Control (N.C.)
Sample 21: GDS23 (0.03125%)
Sample 22: GDS23 (0.0625%)
Sample 23: GDS23 (0.125%)
Sample 24: GDS23 (0.25%)

After the culture, the media were replaced with HBSS(−) (from FUJIFILM Wako Pure Chemical Corporation), and the cells for each sample were divided into cells to be irradiated with UVB (UVB(+)) and cells without irradiation (UVB(−)). For the UVB(+) group, UVB was irradiated at 50 mJ/cm². For the UVB(−) group, only medium exchange was performed. Thereafter, the media were replaced with KB2 media (from Kurabo Industries Ltd.) and the culture was performed at 37° C. under 5% carbon dioxide for 24 hours. Thereafter, a cell viability was measured by the neutral red assay. A cell viability for each sample was calculated assuming that a cell viability for the control (additive-free) in a case of UVB(−) was 100%.

(3-2) Test Results

Figure 7:
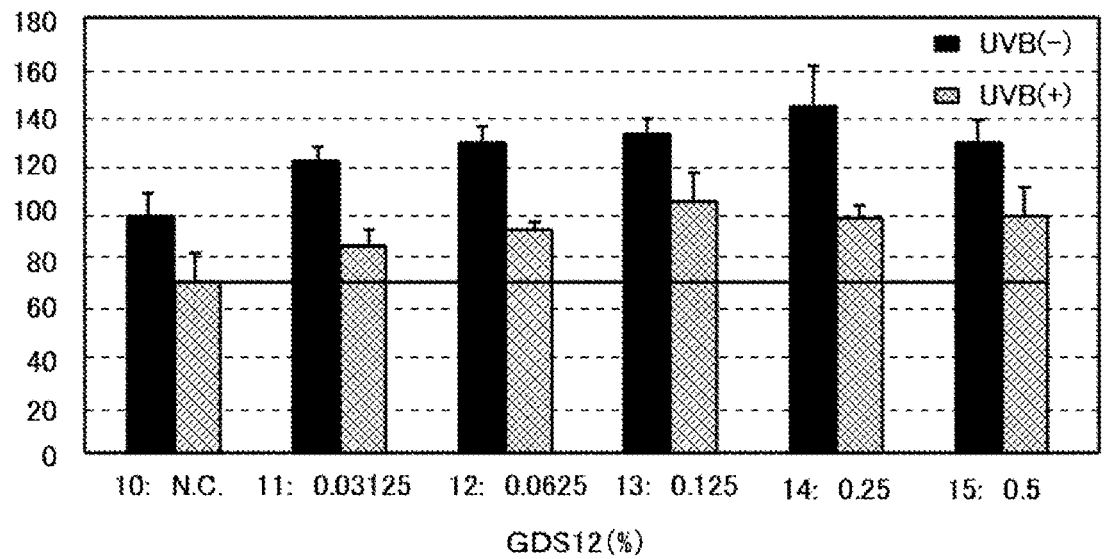
FIG. 7 is a graph illustrating results for Samples 10 to 15 (GDS12)
Figure 8:
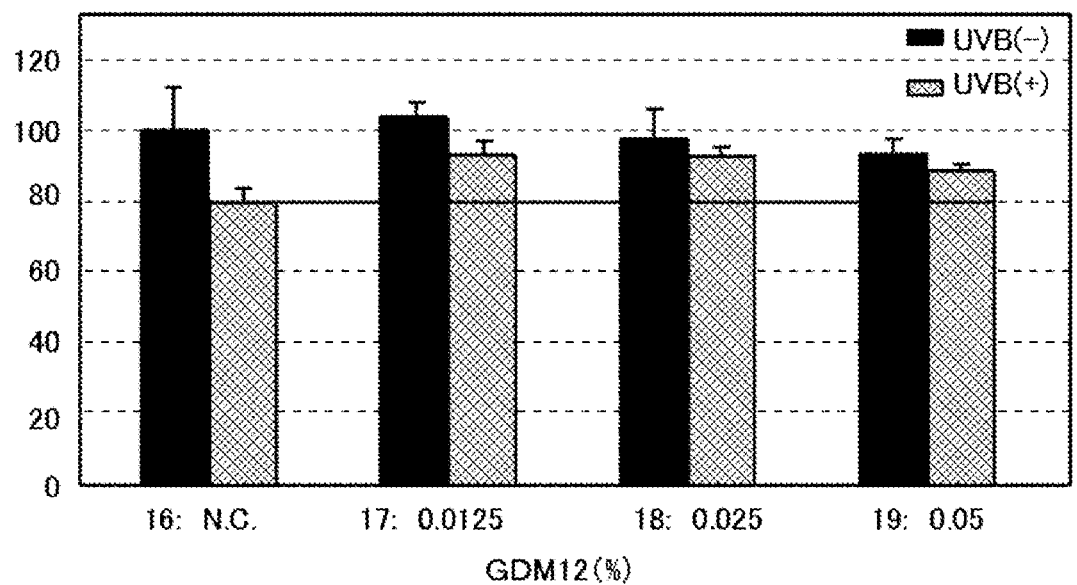
FIG. 8 is a graph illustrating results for Samples 16 to 19 (GDM12)
Figure 9:
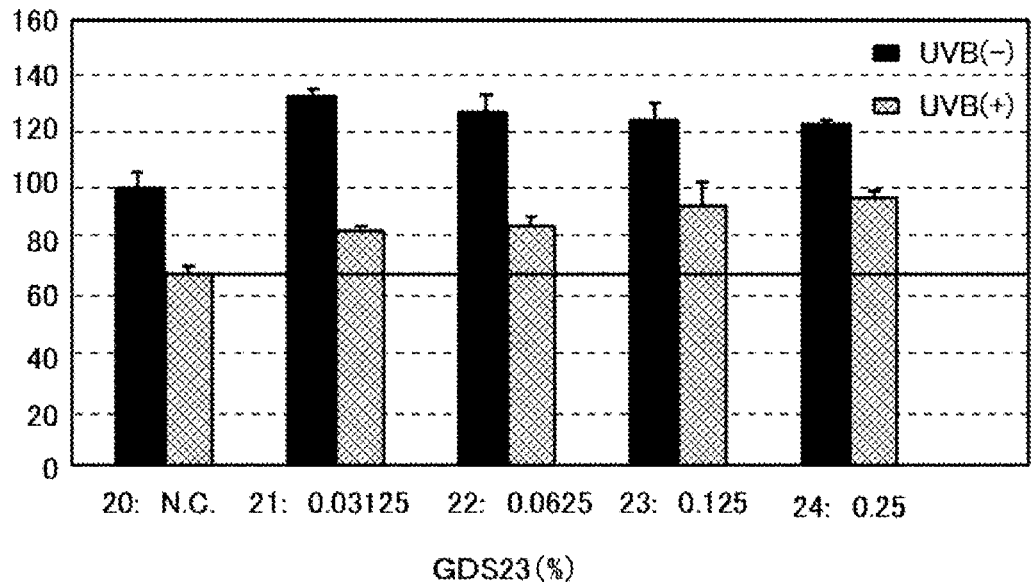
FIG. 9 is a graph illustrating results for Samples 20 to 24 (GDS23)

FIG. 7 is a graph illustrating results for Samples 10 to 15 (GDS12), FIG. 8 is a graph illustrating results for Samples 16 to 19 (GDM12), and FIG. 9 is a graph illustrating results for Samples 20 to 24 (GDS23).

For Samples 10, 16, and 20 as controls, cell viabilities in a case where UVB irradiation was performed (UVB(+)) were reduced as compared with that in a case where UVB irradiation was not performed (UVB(−)) due to cell damage. Also for each sample containing a diacylglycerol PEG adduct, a cell viability in a case of UVB(+) was reduced as compared with that in a case of UVB(−). However, the UVB(+) group of Samples containing the diacylglycerol PEG adduct has a higher cell viability than the control in a case of UVB(+).

Further, when the control in a case of UVB(−) and the UVB(−) group of Samples containing the diacylglycerol PEG adduct are compared with each other, cell viabilities for all Samples are higher than that for the control. This is considered to be because, for each sample containing the diacylglycerol PEG adduct, an antioxidant increased due to oxidative stress other than UVB during 24-hour culture before UVB irradiation.

It was confirmed from these test results that, by applying a diacylglycerol PEG adduct to an epidermis in advance to enhance an antioxidant in the epidermis, it is possible to reduce cell damage due to ultraviolet rays when UVB is irradiated thereafter.

(4) Test 2 of Effect of Suppressing Ultraviolet Damage

Next, a test was conducted to check production rates of prostaglandin E2 and interleukin 1-α, which are inflammatory cytokines causing ultraviolet damage, in order to show an effect of reducing ultraviolet damage by a diacylglycerol PEG adduct.

(4-1) Test Method

Normal human epidermal cells (from Kurabo Industries Ltd.) were seeded at a cell density of $4.0 \times 10^4$ cells/well in a 48-well culture plate using a KG2 medium (from Kurabo Industries Ltd.). Subsequently, the cells were cultured at 37° C. under 5% carbon dioxide for 24 hours. Thereafter, the media were replaced with KB2 media to which Samples 25 to 29, 30 to 34, and 35 to 39 described below were respectively added, and the cells were cultured at 37° C. under 5% carbon dioxide for 24 hours.

Samples 25, 30, and 35 are controls (additive-free and UVB(−)). Samples 26, 31, and 36 are other controls (additive-free and UVB(+)). Samples 27 to 29, 32 to 34, and 37 to 39 are different from one another in the type and/or concentration (mass %, solvent: KB2 medium) of a diacylglycerol PEG adduct, and were all irradiated with UVB.

Sample 25: Control (UVB(−))
Sample 26: Control (UVB(+))
Sample 27: GDM12 (0.005%)
Sample 28: GDM12 (0.01%)
Sample 29: GDM12 (0.05%)
Sample 30: Control (UVB(−))
Sample 31: Control (UVB(+))
Sample 32: GDM12 (0.025%)
Sample 33: GDM12 (0.05%)
Sample 34: GDM12 (0.1%)
Sample 35: Control (UVB(−))
Sample 36: Control (UVB(+))
Sample 37: GDS23 (0.0125%)
Sample 38: GDS23 (0.025%)
Sample 39: GDS23 (0.05%)

After the culture, the media were replaced with HBSS(−) (from FUJIFILM Wako Pure Chemical Corporation), and the UVB(+) group was irradiated with UVB at 20 mJ/cm². For the UVB(−) group, only medium exchange was performed. Thereafter, the media were replaced with KB2 media (from Kurabo Industries Ltd.) again, and the cells were cultured at 37° C. under 5% carbon dioxide for 24 hours. Thereafter, the production quantities of prostaglandin E2 and interleukin 1-α were measured using an assay kit (TaKaRa BCA Protein Assay Kit: from Takara Bio Inc.).

The production rates of prostaglandin E2 (PGE2) and interleukin 1-α (IL1-α) for each sample were calculated from Expressions 1 and 2 described below, assuming that the production rate for the control (additive-free and UVB(−)) was 100%.

$$\text{PGE2 production rate (\%)} = \text{UVB(+)/UVB(−)} \times 100 \quad \text{Expression 1:}$$

$$IL1\text{-}\alpha \text{ production rate (\%)} = \text{UVB(+)/UVB(−)} \times 100 \quad \text{Expression 2:}$$

(4-2) Test Results

Figure 10:
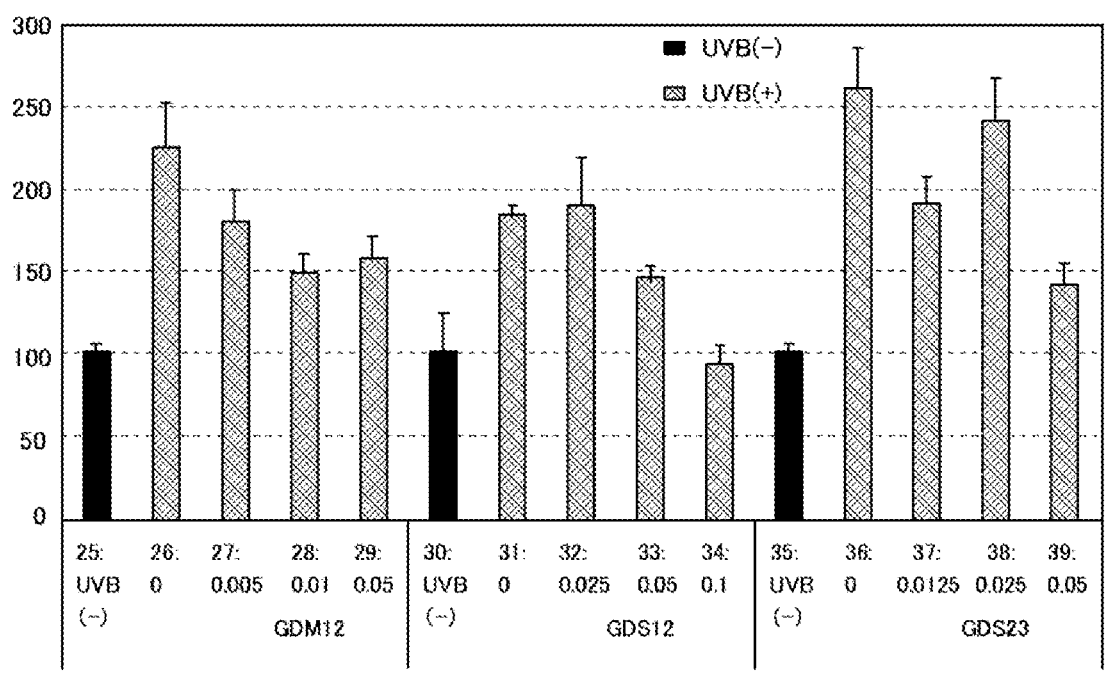
FIG. 10 is a graph illustrating the production rates of prostaglandin E2 for Samples 25 to 39.
Figure 11:
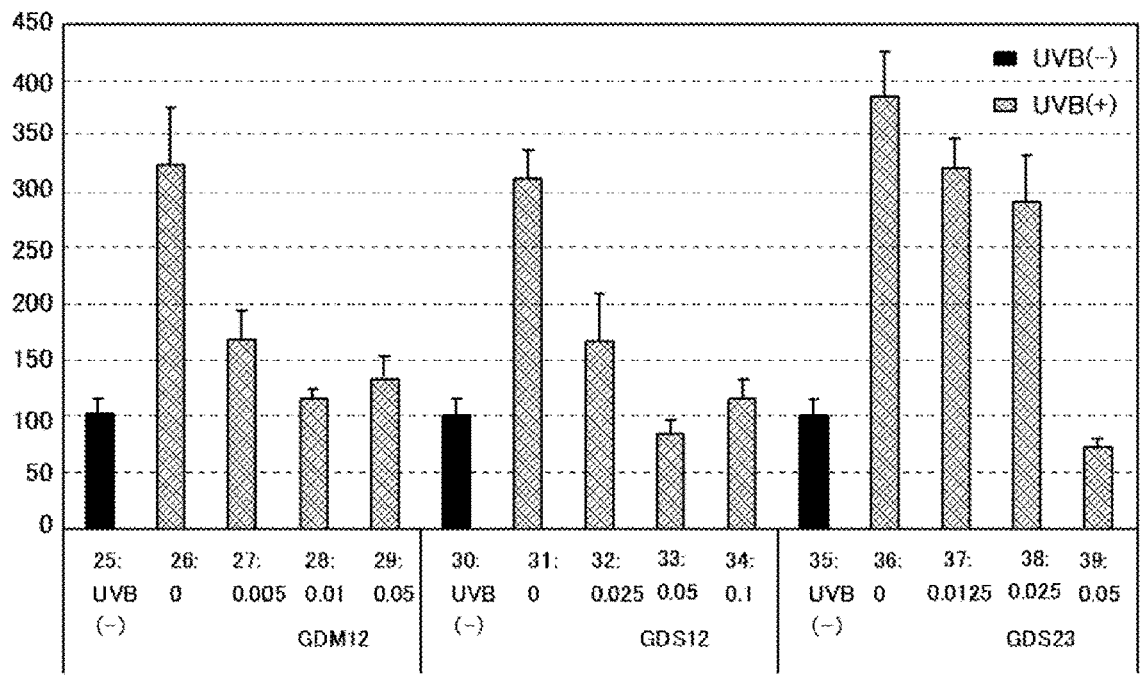
FIG. 11 is a graph illustrating the production rates of interleukin 1-α for Samples 25 to 39.

FIGS. 10 and 11 are graphs illustrating the production rates of prostaglandin E2 and interleukin 1-α for Samples 25 to 39, respectively.

For Samples 26, 31 and 36 without a diacylglycerol PEG adduct, the production rate of inflammatory cytokines is largely increased by UVB irradiation. As compared with those samples, increase in the production rate of inflammatory cytokines by UVB irradiation is suppressed for Samples 27 to 29, 32 to 34, and 37 to 39 with a diacylglycerol PEG adduct added thereto.

It was confirmed from these test results that, by applying a diacylglycerol PEG adduct to an epidermis in advance to enhance an antioxidant in the epidermis, it is possible to suppress production of inflammatory cytokines when UVB is irradiated thereafter.

The results of the tests 1 and 2 of an effect of suppressing ultraviolet damage illustrated in FIGS. 7 to 11 show that the present disclosure can provide an inhibitor for epidermis damage due to ultraviolet rays which uses an expression enhancer for an antioxidant, the expression enhancer containing a diacylglycerol PEG adduct as an active ingredient. Similarly, these test results show that the present disclosure can provide a method for suppressing epidermis damage due to ultraviolet rays, in which a method for enhancing expression of an antioxidant using a diacylglycerol PEG adduct as an active ingredient is applied. This inhibitor or method can be provided in the form of cosmetics or pharmaceuticals.

(5) Test 1 of Effect of Suppressing Air Pollutant Damage

In recent years, there has been reported a concern about health damage due to PM2.5 as air pollutants. The adverse effect of air pollutants on the human body is that active oxygen is generated and damages cells and organs. It is considered that health damage due to exposure to air pollutants can be reduced by enhancing an antioxidant function in the body which is originally possessed by humans in order to counter the air pollutant damage. Therefore, a test was conducted to check a relation between contact with DPE (Diesel Particle Extracts) as air pollutant mimics and the protein quantity in cells in order to show an effect of reducing air pollutant damage, provided by a diacylglycerol PEG adduct enhancing expression of an antioxidant in an epidermis.

(5-1) Test Method

Normal human epidermal cells (from Kurabo Industries Ltd.) were seeded at a cell density of $2.0 \times 10^4$ cells/well in a 96-well culture plate using a KG2 medium (from Kurabo Industries Ltd.). Subsequently, the cells were cultured at 37° C. under 5% carbon dioxide for 24 hours. Thereafter, the media were replaced with KB2 media to which Samples 40 to 46 described below were respectively added, and then the culture was performed at 37° C. under 5% carbon dioxide for 24 hours.

Sample 40 is a control (additive-free). Samples 41 to 46 are different from one another in the type and/or concentration (mass %, solvent: KB2 medium) of a diacylglycerol PEG adduct.

Sample 40: Control (N.C.)
Sample 41: GDS23 (0.0005%)
Sample 42: GDS23 (0.001%)
Sample 43: GDS23 (0.002%)
Sample 44: GDM12 (0.001%)
Sample 45: GDM12 (0.002%)
Sample 46: GDM12 (0.004%)

After the culture, the medium for each sample was replaced with two media, that is, a DPE-free KB2 medium and a KB2 medium containing 5% DPE, and the culture was performed at 37° C. under 5% carbon dioxide for 24 hours. Thereafter, the protein quantity in cells was measured using an assay kit (TaKaRa BCA Protein Assay Kit: from Takara Bio Inc.).

(5-2) Test Results

Figure 12:
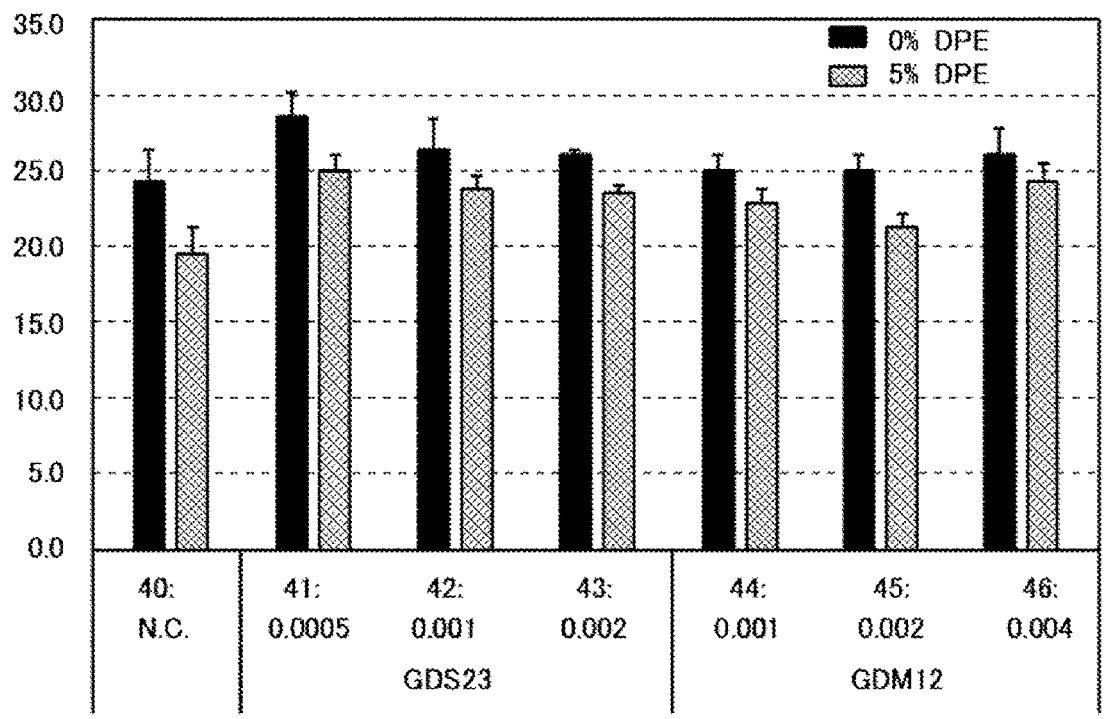
FIG. 12 is a graph illustrating measurement results of the protein quantities for Samples 40 to 46.

FIG. 12 is a graph illustrating measurement results of the protein quantities for Samples 40 to 46. In a DPE-free group, there is no significant difference between Sample 40 as a control and a group with a diacylglycerol PEG adduct of Samples 41 to 46. That is, this result shows that addition of the diacylglycerol PEG adduct does not affect the protein quantity in cells, that is, the diacylglycerol PEG adduct has no cytotoxicity.

In a group with 5% DPE added, the protein quantity in cells is largely reduced (the cells are damaged) for Sample 40 as a control, but reduction in the protein quantity is suppressed in the group with the diacylglycerol PEG adduct of Samples 41 to 46. Accordingly, it was confirmed that, by adding a diacylglycerol PEG adduct in advance to enhance an antioxidant in an epidermis in a living organism, cell damage by DPE when cells came into contact with DPE thereafter was reduced.

(6) Test 2 of Effect of Suppressing Air Pollutant Damage

Next, a test was conducted to check contact with DPE (Diesel Particle Extracts) as air pollutant mimics and the production rates of prostaglandin E2 and interleukin 1-α as inflammatory cytokines causing cell damage.

(6-1) Test Method

Normal human epidermal cells (from Kurabo Industries Ltd.) were seeded at a cell density of $2.0 \times 10^4$ cells/well in a 96-well culture plate using a KG2 medium (from Kurabo Industries Ltd.). Subsequently, the cells were cultured at 37° C. under 5% carbon dioxide for 24 hours. Thereafter, the media were replaced with KB2 media to which Samples 47 to 53 described below were respectively added, and the cells were cultured at 37° C. under 5% carbon dioxide for 24 hours.

Sample 47 is a control (additive-free). Samples 48 to 53 are different from one another in the type and/or concentration (mass %, solvent: KB2 medium) of a diacylglycerol PEG adduct.

Sample 47: Control (N.C.)
Sample 48: GDS23 (0.0005%)
Sample 49: GDS23 (0.001%)
Sample 50: GDS23 (0.002%)
Sample 51: GDM12 (0.001%)
Sample 52: GDM12 (0.002%)
Sample 53: GDM12 (0.004%)

After the culture, the medium for each sample was replaced with two media, that is, a DPE-free KB2 medium and a KB2 medium containing 5% DPE, and the culture was performed at 37° C. under 5% carbon dioxide for 24 hours. Thereafter, using an assay kit (TaKaRa BCA Protein Assay Kit: from Takara Bio Inc.), the protein quantity was measured, and the production quantities of prostaglandin E2 and interleukin 1-α were also measured by the ELISA method. The production quantities of prostaglandin E2 and interleukin 1-α were converted per protein quantity.

(6-2) Test Results

Figure 13:
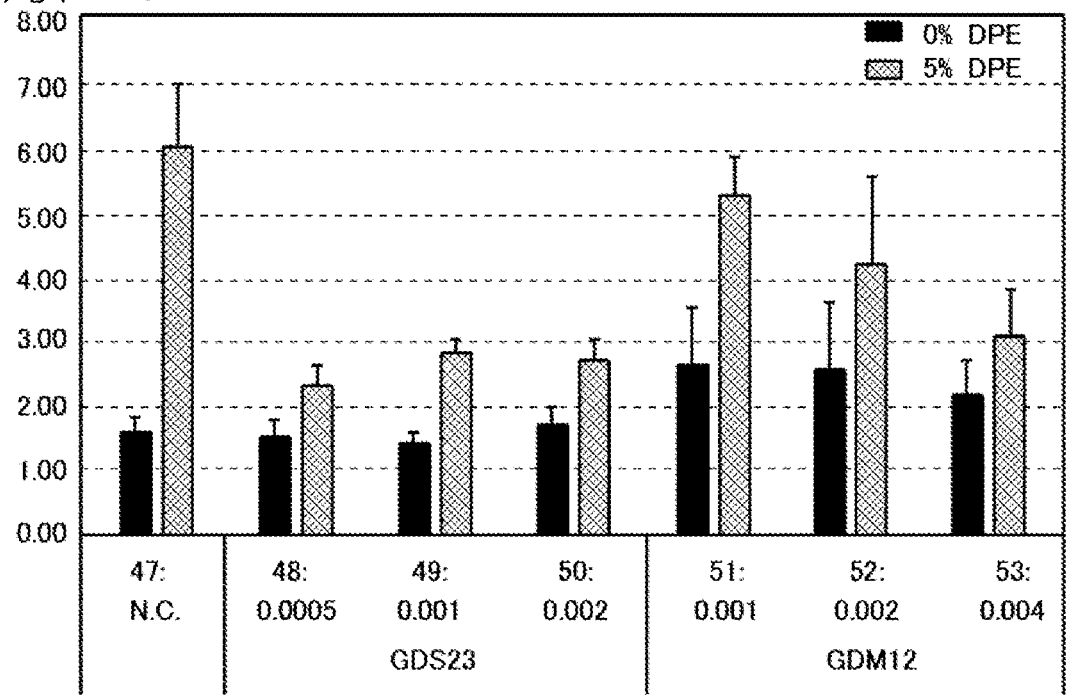
FIG. 13 is a graph illustrating the production quantities of prostaglandin E2 for Samples 47 to 53.
Figure 14:
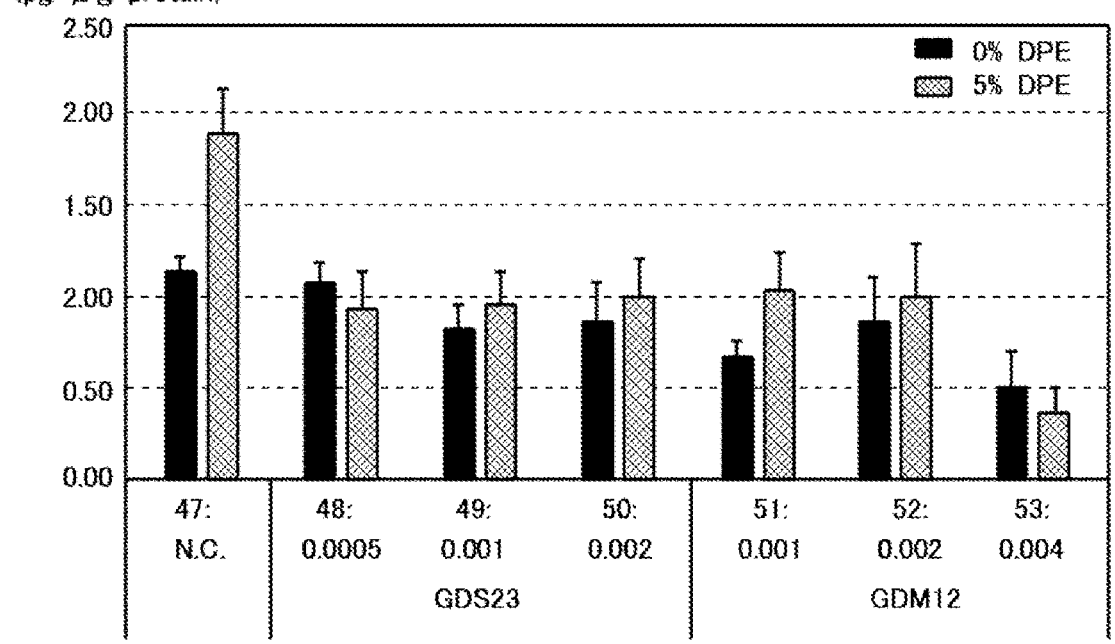
FIG. 14 is a graph illustrating the production quantities of interleukin 1-α for Samples 47 to 53.

FIGS. 13 and 14 are graphs illustrating the production quantities of prostaglandin E2 and interleukin 1-α for Samples 47 to 53, respectively.

For Sample 47 without a diacylglycerol PEG adduct, the production quantity of inflammatory cytokines is largely increased by DPE. As compared with that sample, increase in the production quantity of inflammatory cytokines by DPE is suppressed for Samples 48 to 53 with the diacylglycerol PEG adduct added thereto.

It was confirmed from these test results that, by applying a diacylglycerol PEG adduct to an epidermis in advance to enhance an antioxidant in the epidermis, it is possible to suppress production of inflammatory cytokines when the epidermis comes into contact with DPE thereafter.

The results of the tests 1 and 2 of an effect of suppressing air pollutant damage illustrated in FIGS. 12 to 14 show that the present disclosure can provide an inhibitor for epidermis damage due to air pollutants which uses an expression enhancer for an antioxidant, the expression enhancer containing a diacylglycerol PEG adduct as an active ingredient. Similarly, these test results show that the present disclosure can provide a method for suppressing epidermis damage due to air pollutants, in which a method for enhancing expression of an antioxidant using a diacylglycerol PEG adduct as an active ingredient is applied. This agent or method can be provided in the form of cosmetics or pharmaceuticals.

(7) Test of Effect of Suppressing Hydroquinone Oxidation

Hydroquinone (HQ) is a substance generally used in a skin preparation for external use such as cream and ointment prescribed by aesthetic medical institutions around the world. Although the skin-whitening effect of hydroquinone has been reported since the 1950s, many doctors in Japan avoid it due to side effect issues. In Japan, prescription was permitted only under the control of doctors until 2001, but after relaxation of regulations in the same year, hydroquinone was permitted to be formulated into cosmetics. However, there is still little information on the clear mechanism of action and safety of hydroquinone with respect to skin whitening, and its side effects such as skin dryness, erythema, and contact dermatitis are issues. As represented by the following chemical reaction formula, it is considered that cytotoxicity and toxicity as causes of the side effects are enhanced by benzoquinone (BQ) to be generated by oxidation of hydroquinone. The oxidation-reduction reaction between hydroquinone and benzoquinone is an equilibrium reaction.

[Chemical formula 3]

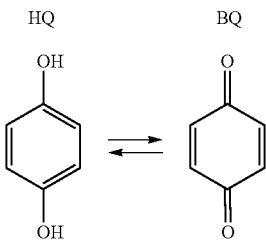

Therefore, it is considered that if oxidation of hydroquinone is suppressed by increasing the antioxidative activity of cells themselves, cytotoxicity can be reduced, leading to suppression of the side effects.

(7-1) Test to Check Cytotoxicity of Hydroquinone and Benzoquinone

First, a test was conducted to check a difference of cytotoxicity between hydroquinone and benzoquinone.

Test Method

Normal human epidermal melanocytes (NHEM: from Kurabo Industries Ltd.) were seeded at a cell density of $2.0 \times 10^4$ cells/well in a 96-well culture plate using a medium (DermaLife (registered trademark) M Comp kit medium: from Kurabo Industries Ltd.). Subsequently, the cells were cultured at 37° C. under 5% carbon dioxide for 24 hours. Thereafter, the media were replaced with the same type of media each containing hydroquinone (HQ) or benzoquinone (BQ) in a predetermined amount (0 μM, 62.5 μM, 125 μM, 250 μM, or 500 μM), and the cells were cultured at 37° C. under 5% carbon dioxide for 24 hours. After the culture, a cell viability was measured by the neutral red assay. A cell viability of each sample with HQ or BQ added thereto was calculated assuming that a cell viability of an additive-free control (N.C.) was 100%.

Test Results

Figure 15:
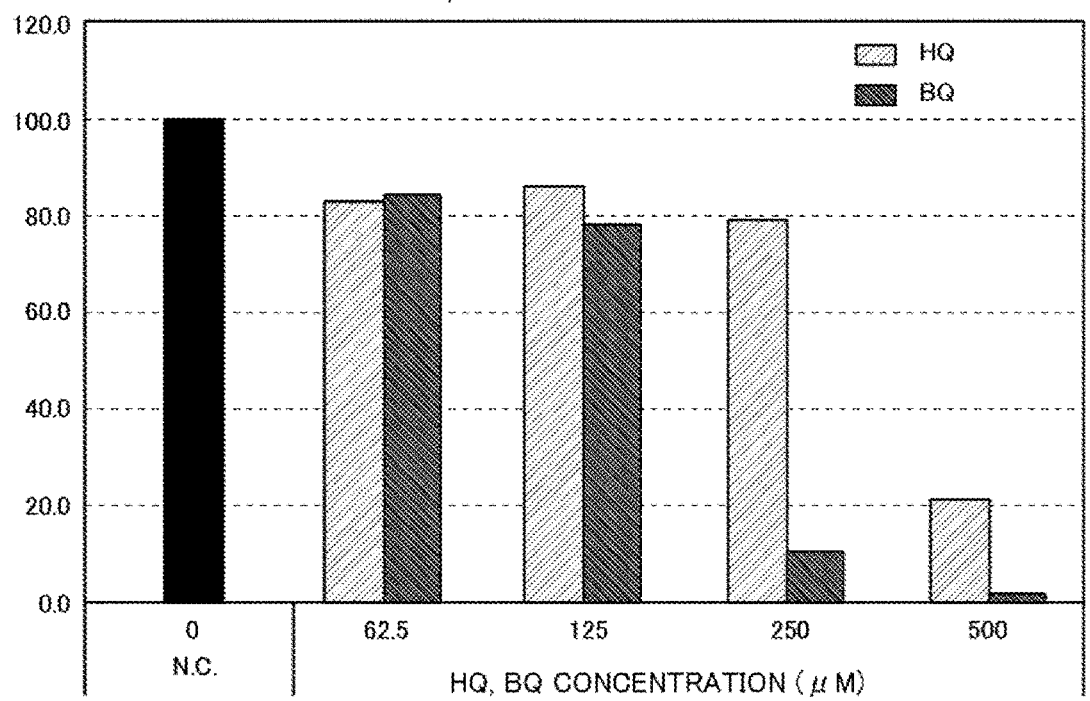
FIG. 15 is a graph illustrating test results on cytotoxicity of hydroquinone and benzoquinone.

FIG. 15 is a graph illustrating test results on cytotoxicity of hydroquinone and benzoquinone. Hydroquinone was found not to be cytotoxic even at 250 μM, whereas benzoquinone was found to exhibit cytotoxicity (cell toxicity) at 250 μM. Therefore, it can be said that benzoquinone is more toxic and injurious than hydroquinone.

(7-2) Test to Check Cytotoxicity of Hydroquinone

Next, a test was conducted to check cytotoxicity in a case where hydroquinone was maintained without being oxidized into benzoquinone.

Test Method

The oxidation-reduction reaction between hydroquinone and benzoquinone is an equilibrium reaction, and hydroquinone is easily oxidized to benzoquinone. Therefore, as represented by the following chemical reaction formula, sodium pyrosulfite (an antioxidant generally used also in foods and the like) was dissolved in a medium in combination with hydroquinone to suppress oxidation of hydroquinone, and cytotoxicity was evaluated by an identical test method to that in the above section. A control (N.C.) is an additive-free sample, and all other samples contain 0.5 μM of sodium pyrosulfite and are different from one another in the amount of hydroquinone.

[Chemical formula 4]

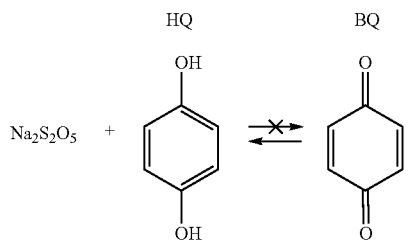

Test Results

Figure 16:
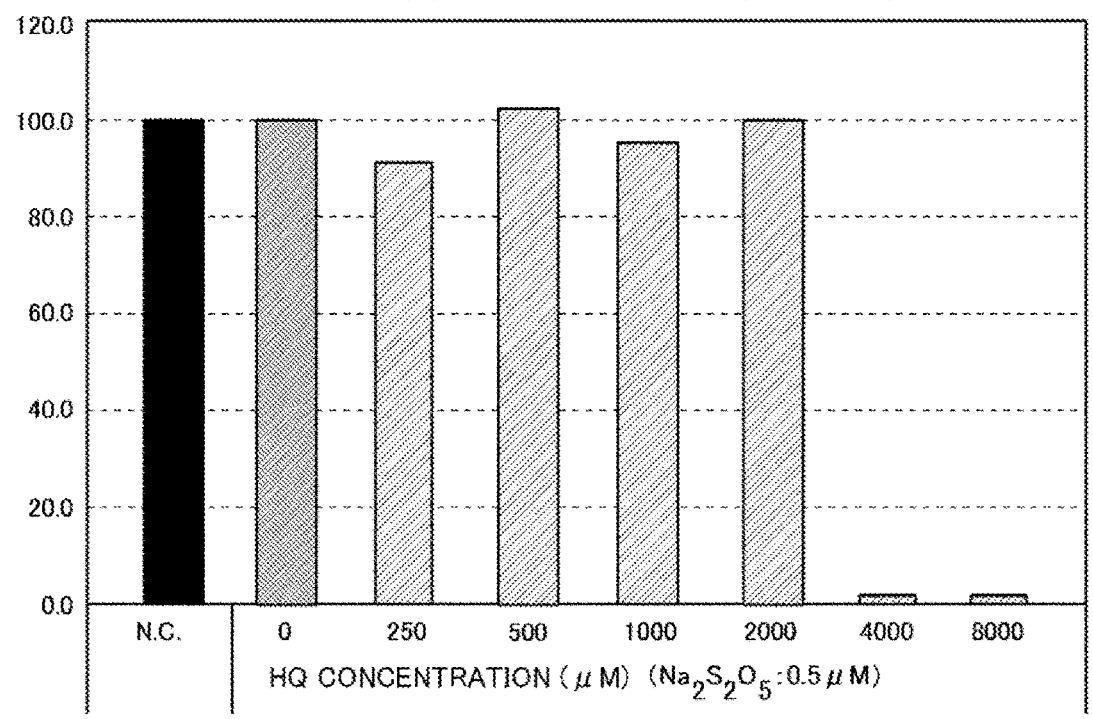
FIG. 16 is a graph illustrating test results on cytotoxicity of hydroquinone.

FIG. 16 is a graph illustrating test results on cytotoxicity of hydroquinone. There was no difference between a sample containing sodium pyrosulfite only and a control. For samples containing sodium pyrosulfite and hydroquinone, cytotoxicity was not found up to 2000 μM of hydroquinone. On the other hand, in FIG. 15 referred to in the above section, cytotoxicity was found for 500 μM of hydroquinone, and it is considered that oxidation of hydroquinone occurred. From this result, it is considered that, unless hydroquinone is oxidized in cells, cytotoxicity can be reduced and side effects caused by benzoquinone can be also suppressed.

(8) Cytotoxicity Suppression Test 1 of Hydroquinone

A test was conducted to check whether an effect of suppressing oxidation of hydroquinone, that is, an effect of suppressing cytotoxicity was obtained by the action of enhancing expression of an antioxidant in an epidermis by a diacylglycerol PEG adduct.

(8-1) Test Method

Normal human epidermal melanocytes (NHEM: from Kurabo Industries Ltd.) were seeded at a cell density of $2.0 \times 10^4$ cells/well in a 96-well culture plate using a medium (DermaLife (registered trademark) M Comp kit medium: from Kurabo Industries Ltd.). Subsequently, the cells were cultured at 37° C. under 5% carbon dioxide for 24 hours. Thereafter, the media were replaced with media to which Samples 54 to 58 described below were respectively added, and the cells were cultured at 37° C. under 5% carbon dioxide for 6 hours.

Sample 54 is a control (both hydroquinone and GDS23 are not added). Sample 56 is another control (only 300 µM of hydroquinone is added). Samples 56, 57 and 58 contain 300 µM of hydroquinone and different amounts of GDS23.
  Sample 54: Control (N.C.)
  Sample 55: Control (HQ only)
  Sample 56: GDS23 (500 µM, HQ)
  Sample 57: GDS23 (1000 µM, HQ)
  Sample 58: GDS23 (2000 µM, HQ)

After the culture, a cell viability was measured by the neutral red assay. A cell viability for each sample was calculated assuming that a cell viability for the additive-free control (N.C.) was 100%.

(8-2) Test Results

Figure 17:
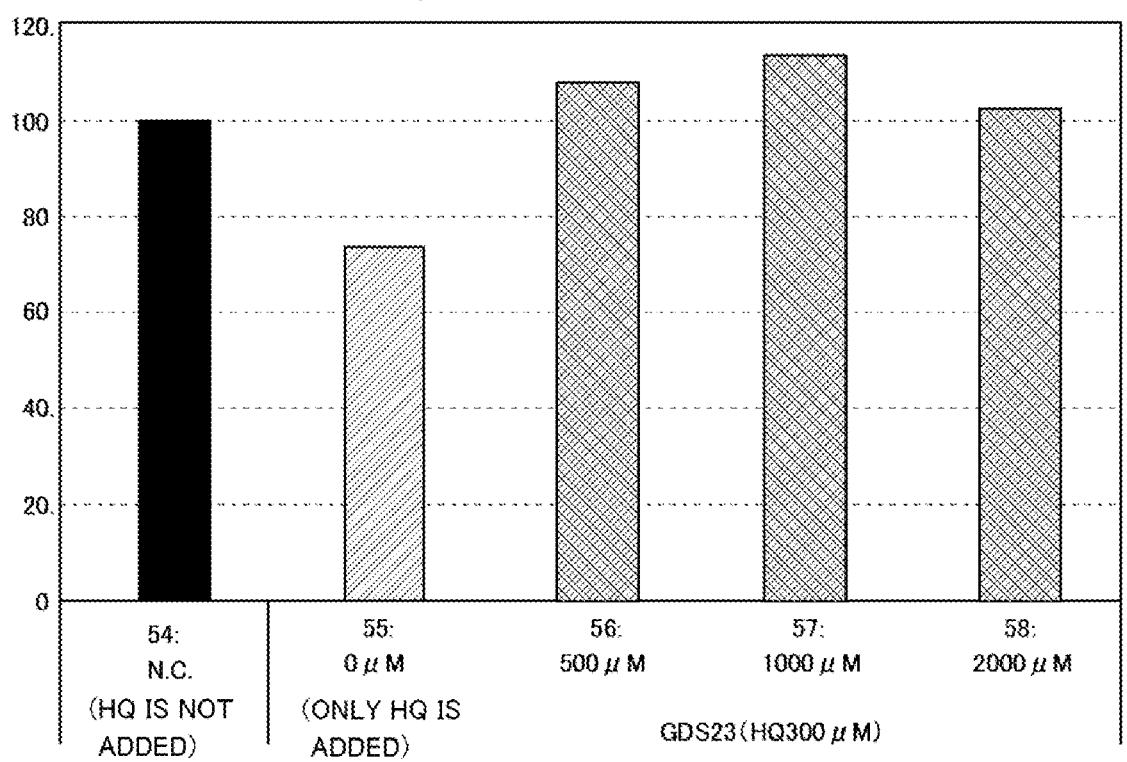
FIG. 17 is a graph illustrating measurement results of cell viabilities for Samples 54 to 58.

FIG. 17 is a graph illustrating measurement results of cell viabilities for Samples 54 to 58. With regard to Samples 56 to 58 containing 300 µM of hydroquinone and a diacylglycerol PEG adduct, substantially the same cell viability was obtained as that with regard to Sample 54 as a control. Therefore, it is considered that hydroquinone was maintained without being oxidized in Samples 56 to 58.

It was confirmed from these test results that, by enhancement of an antioxidant in a living organism by a diacylglycerol PEG adduct in advance, oxidation of hydroquinone in cells was able to be suppressed after administration of hydroquinone and cell damage was prevented.

(9) Cytotoxicity Suppression Test 2 of Hydroquinone

In order to check an effect of suppressing hydroquinone oxidation in an epidermis by a diacylglycerol PEG adduct, a test was conducted in which hydroquinone was increased as compared with the above test (8).

(9-1) Test Method

A cell viability was measured by the same test method as (8-1) described above. However, Samples 59 to 62 described below were used as samples to be added to media. Sample 59 is a control (both hydroquinone and GDS23 are not added). Sample 60 is another control (only 400 µM of hydroquinone is added). Sample 61 contains 400 µM of hydroquinone and 500 µM of GDS23. Sample 62 contains 400 µM of hydroquinone, 500 µM of GDS23, squalane, and cholesterol.
  Sample 59: Control (N.C.)
  Sample 60: Control (HQ only)
  Sample 61: GDS23 (500 µM, HQ)
  Sample 62: GDS23 (500 µM, HQ, squalane, and cholesterol)

Sample 62 was added to a medium in the form of refined vesicles. The refined vesicles were prepared in the following manner. A 10 mL of medium (DermaLife (registered trademark) M Comp kit medium: from Kurabo Industries Ltd.) was added at 80° C. to a mixture in which 163.8 mg of GDS23, 122.85 mg of squalane, and 16.38 mg of cholesterol were dissolved at 80° C., was mixed and stirred, was cooled to room temperature, and was diluted to a predetermined concentration. Among the vesicles obtained by this preparation method, 97.3% had diameters in a range of 20 to 40 nm. In general, for example, the average diameters of vesicles self-formed in a 2% aqueous solution of GDM12 and a 2% aqueous solution of GDS23 are both about 140 nm.

(9-2) Test Results

Figure 18:
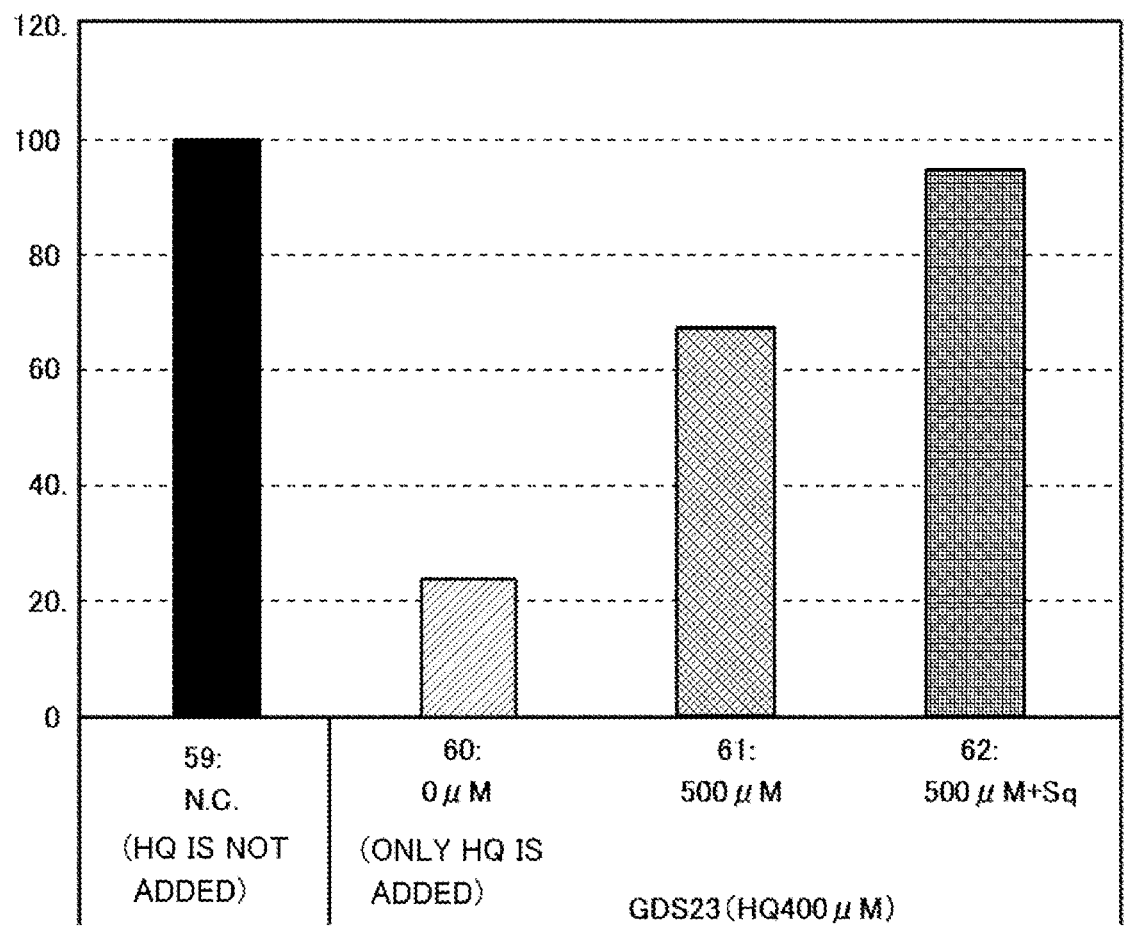
FIG. 18 is a graph illustrating measurement results of cell viabilities for Samples 59 to 62.

FIG. 18 is a graph illustrating measurement results of cell viabilities for Samples 59 to 62. When Sample 61 is compared with Sample 56 in FIG. 17, the cell viability is reduced because hydroquinone is increased. However, Sample 61 also shows a higher cell viability than Sample 60 containing hydroquinone only.

In particular, for Sample 62 containing refined vesicles, substantially the same cell viability was obtained as that for Sample 59 as a control. Therefore, it is considered that uptake of a diacylglycerol PEG adduct into cells is further improved by mixing it with another lipid to form refined vesicles, rather than by using the diacylglycerol PEG adduct only.

The results of the tests 1 and 2 of suppressing cytotoxicity of hydroquinone illustrated in FIGS. 17 and 18 show that the present disclosure can provide an oxidation inhibitor of hydroquinone in an epidermis which uses an expression enhancer for an antioxidant, the expression enhancer containing a diacylglycerol PEG adduct as an active ingredient. Similarly, these test results show that the present disclosure can provide a method for suppressing oxidation of hydroquinone in an epidermis, in which a method for enhancing expression of an antioxidant using a diacylglycerol PEG adduct as an active ingredient is applied. This inhibitor or method can be provided in the form of cosmetics or pharmaceuticals.

Illustrative Combinations and Additional Examples

This section describes additional aspects and features of systems and methods for enhancing the expression of an antioxidant in an epidermis, presented without limitation as a series of paragraphs. Each of these paragraphs can be combined with one or more other paragraphs, and/or with disclosure from elsewhere in this application, in any suitable manner.

A0. A method for enhancing expression of an antioxidant in an epidermis, comprising applying a diacylglycerol PEG adduct to a human epidermis as an active ingredient, wherein the diacylglycerol PEG adduct is represented by

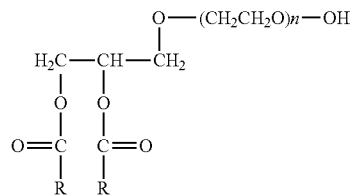

where number of carbons in R in a long-chain fatty acid is in a range of 11 to 23 and n in a polyethylene glycol chain is in a range of 11 to 46.

A1. The method of A0, wherein the diacylglycerol PEG adduct is selected from the group consisting of PEG-12 glycerol dimyristate (GDM12), PEG-12 glycerol distearate (GDS12), PEG-23 glycerol distearate (GDS23), PEG-23 glycerol dipalmitate (GDP23), and PEG-12 glycerol dioleate (GDO12).

A2. The method of A0 or A1, wherein the diacylglycerol PEG adduct permeates an epidermis in a solution state.

A3. The method of A0 or A1, wherein the diacylglycerol PEG adduct permeates an epidermis in a vesicle state.

A4. The method of A3, wherein vesicles of the diacylglycerol PEG adduct have diameters in a range of 20 to 40 nm.

A5. The method of A0 or A1, wherein the antioxidant is an oxidative stress response gene, and the oxidative stress response gene is Nrf-2.

A6. The method of A0 or A1, wherein the antioxidant is an oxidative stress response gene, and the oxidative stress response gene is PPARG.

A7. The method of A0 or A1, wherein the antioxidant is an antioxidant enzyme, and the antioxidant enzyme is one or more of the group consisting of NAD(P)H quinone reductase (NQO-1), catalase (CAT)), and heme oxygenase-1 (HMOX1).

A8. The method of A0 or A1, wherein the antioxidant is an antioxidant protein, and the antioxidant protein is glutathione.

A9. The method of A0 or A1, wherein the diacylglycerol PEG adduct is one of ingredients of cosmetics or pharmaceuticals, and the method further comprises applying the cosmetics or pharmaceuticals on a surface of a human skin.

B0. A method for suppressing epidermis damage caused by ultraviolet rays, using the method according to A0 or A1.

C0. A method for suppressing epidermis damage caused by air pollutants, using the method according to A0 or A1.

D0. A method for suppressing oxidation of hydroquinone in an epidermis, using the method according to A0 or A1.

CONCLUSION

The disclosure set forth above may encompass multiple distinct examples with independent utility. Although each of these has been disclosed in its preferred form(s), the specific embodiments thereof as disclosed and illustrated herein are not to be considered in a limiting sense, because numerous variations are possible. To the extent that section headings are used within this disclosure, such headings are for organizational purposes only. The subject matter of the disclosure includes all novel and nonobvious combinations and subcombinations of the various elements, features, functions, and/or properties disclosed herein. The following claims particularly point out certain combinations and subcombinations regarded as novel and nonobvious. Other combinations and subcombinations of features, functions, elements, and/or properties may be claimed in applications claiming priority from this or a related application. Such claims, whether broader, narrower, equal, or different in scope to the original claims, also are regarded as included within the subject matter of the present disclosure.

The invention claimed is:

1. A method for enhancing expression of an antioxidant in an epidermis, the method comprising:
applying a diacylglycerol PEG adduct to a human epidermis as an active ingredient, wherein the diacylglycerol PEG adduct is represented by

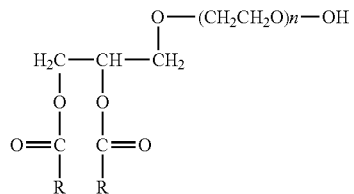

wherein a number of carbons in R in a long-chain fatty acid is in a range of 11 to 23 and n in a polyethylene glycol chain is in a range of 11 to 46; and wherein the diacylglycerol PEG adduct is selected from the group consisting of PEG-12 glycerol dimyristate (GDM12), PEG-12 glycerol distearate (GDS12), PEG-23 glycerol distearate (GDS23), PEG-23 glycerol dipalmitate (GDP23), and PEG-12 glycerol dioleate (GDO12).

2. The method according to claim 1, wherein the diacylglycerol PEG adduct is configured to permeate an epidermis in a solution state.

3. The method according to claim 1, wherein the diacylglycerol PEG adduct is configured to permeate an epidermis in a vesicle state.

4. The method according to claim 1, wherein the antioxidant is an oxidative stress response gene, and the oxidative stress response gene is Nrf-2.

5. The method according to claim 1, wherein the antioxidant is an oxidative stress response gene, and the oxidative stress response gene is PPARG.

6. The method according to claim 1, wherein the antioxidant includes one or more antioxidant enzymes selected from the group consisting of NAD(P)H quinone reductase (NQO-1), catalase (CAT)), and heme oxygenase-1 (HMOX1).

7. The method according to claim 1, wherein the antioxidant is an antioxidant protein, and the antioxidant protein is glutathione.

8. The method according to claim 3, wherein vesicles of the diacylglycerol PEG adduct have diameters in a range of 20 to 40 nm.

9. The method according to claim 1, wherein the diacylglycerol PEG adduct is one of ingredients of cosmetics or pharmaceuticals, and the method further comprises applying the cosmetics or pharmaceuticals on a surface of a human skin.

10. A method for suppressing epidermis damage caused by ultraviolet rays, using the method according to claim 1.

11. A method for suppressing epidermis damage caused by air pollutants, using the method according to claim 1.

12. A method for suppressing oxidation of hydroquinone in an epidermis, using the method according to claim 1.

* * * * *